US006431874B1

(12) United States Patent
Szynalski

(10) Patent No.: US 6,431,874 B1
(45) Date of Patent: Aug. 13, 2002

(54) STOP SMOKING METHOD AND COMPOSITION

(75) Inventor: Alexander Goen Szynalski, Randolph, NJ (US)

(73) Assignee: Goen Corporation, Cedar Knolls, NJ (US)

( * ) Notice: Subject to any disclaimer, the term of this patent is extended or adjusted under 35 U.S.C. 154(b) by 0 days.

(21) Appl. No.: 09/427,447

(22) Filed: Oct. 27, 1999

(51) Int. Cl.[7] .............................................. G09B 23/28
(52) U.S. Cl. ....................................................... 434/262
(58) Field of Search ................................ 514/282, 343; 424/449; 434/262

(56) References Cited

U.S. PATENT DOCUMENTS 5,055,478 A * 10/1991 Cooper et al. .............. 514/343
5,414,005 A * 5/1995 Schneider et al. .......... 514/343
5,780,051 A * 7/1998 Eswara et al. .............. 424/449
5,965,567 A * 10/1999 Archer et al. ............... 514/282

FOREIGN PATENT DOCUMENTS

GB          1017032        1/1966

* cited by examiner

*Primary Examiner*—Sam Rimell
(74) *Attorney, Agent, or Firm*—Pharmaceutical Patent Law, LLC; Mark Pohl

(57) ABSTRACT

The inventor discloses a unique, new and useful process to reduce tobacco smoking, entitled Stop Smoking Method and Composition, consisting of: (1) educating tobacco smokers regarding smoking, its physiological dangers and addictive nature, and techniques to stop smoking; (2) hypnotizing said tobacco smokers, and (3) providing dietary substances to address the nutritional needs of nicotine addiction and the nutritional challenges thereof.

8 Claims, No Drawings

STOP SMOKING METHOD AND COMPOSITION

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND

The prior art discloses many stop-smoking products and methods including, for example; (A) education to educate smokers regarding smoking, its physiological dangers and addictive nature, and conscious techniques to stop smoking; (B) hypnosis, to use the unconscious mind to stop smoking; and (C) nutritional supplements, addressing the nutritional challenges with regard to stopping smoking.

SUMMARY

While using each one of these three elements is known in the art, I have found that by combining all of these three elements together, they act on the three areas most important for stopping smoking—the conscious mind, the unconscious mind, and the body—and are synergistically effective in helping people to stop smoking.

This synergy was unexpected. I am a Certified Hypnotist and am a Nutritionist, with over twenty years experience in the fields of hypnosis, seminar presentation and nutrition. I am a member of the American Association of Professional Hypnotherapists, the National Guild of Hypnotists, the International Association of Counselors and Therapists, and am certified by the Hypnodyne Foundation. I am listed in *Who's Who in Executives and Professionals*, and I was a finalist for the 1999 Ernst & Young Entrepreneur of the Year award. I have been a special guest on numerous national television and radio programs, and was featured on the #1 television fitness show in the country. I maintain a practice in Cedar Knolls, N.J. I have successfully used hypnosis in many types of situations. I have, for example, worked with athletes to improve their athletic performance, and have worked with corporations as a sales and personal-development trainer. I am driven by a sincere passion for helping people maximize their personal potential and overcome addictions to smoking and food. I enjoy a reputation for extremely high success through my seminars.

DETAILED DESCRIPTION

My invention therefore comprises three elements: (1) education for the conscious mind regarding smoking, its physiological dangers and addictive nature, and techniques to stop smoking; (2) hypnosis for the unconscious mind, which hypnosis addresses the unconscious mind and its way of affecting behavior; and (3) dietary substances, to address the physiological needs of a person entailed in stopping smoking.

Education. The first element of my invention is education regarding smoking. This educational process can include addressing the benefits of a regular exercise program. Thus, the educational materials or program educates the smoker to engage in some form of light exercise. Not only will exercise help clear the body of the toxins acquired through smoking, but exercise will also help release endorphins which relieve stress as well as making you feel good. Exercise will rapidly reverse the damage done to the body from smoking. If the smoker has not engaged in exercise for a long time, or the smoker has a weight problem or any other health problem, the smoker should consult their physician before starting any regimen of exercise.

In addition to this, I have found that in my preferred embodiment of my invention, the education program also addresses the physiological progression of smoking, its physiological dangers and addictive nature, and some conscious techniques to stop smoking. ©1999

The physiological progression of smoking entails three discreet steps. Knowing these steps helps the smoker recognize them as they occur, and thus recognize the needs they fill.

Stage 1—Light a cigarette and inhale. This takes about 7 seconds. The deep breath of the inhale increases the flow of blood and oxygen to the heart and you feel more relaxed (not due to the cigarette, but due to the deep breath).

Stage 2—Seven seconds to fifteen minutes later, nicotine enters the liver, which in turn releases sugar into the bloodstream. This results in a physical uplift (not from the cigarette, but from the release of sugar into the bloodstream) which then in turn causes the pancreas to release insulin into the bloodstream. This gives you an energy boost. Normally, it is a temporary energy boost because the muscle cells of the body are resistant to insulin. So what happens is that your energy level goes up and then crashes, all over again. In fifteen minutes, you want to start smoking again due to the tense feelings you experience from your energy level being reduced. What we suggest is for you to sensitize your body to insulin. Before we suggest how you do this, you first should study the two diagrams pictured below. To better understand this phenomenon, we will provide an in-depth clarification of the diagrams.

Stage 3—Fifteen to twenty minutes after beginning to smoke, the nicotine interrupts the normal transmission of neurons by competing with acetylcholine at the nerve terminal, producing such effects as an increased heart rate and respiration, along with feelings of tension and of being "wired up." It also increases arousal and a sense of well-being and focused attention. A side benefit to understanding this step is to take proper nutrients so you do not allow this physical and physiological progression of smoking to occur. This will help with maintaining or even reducing weight and increasing lean muscle tissue.

In my preferred embodiment, the smoker is educated on the physiological dangers and addictive nature of smoking. These dangers are now so widely known as to not need to be discussed in detail here.

In my preferred embodiment, the person is educated on the benefits of modifying their daily diet. This addresses potential weight gain problems, one of the biggest fears of smokers.

Regarding potential weight gain, why do we gain weight when we stop smoking? Muscle cells become more sensitive to insulin. In my preferred embodiment, therefore, I recommend:

Avoid refined carbohydrates. All carbohydrates start out in their rarest edible form as complex, but we make them refined by processing, preserving, storing, drying, and cooking.

Increase physical activity, especially five to fifteen minutes after meals.

Take 100 micrograms of chromium along with the proper cofactors, one half hour before each meal with a full glass of water. The product containing chromium (CHROMIUM CHELAVITE™) that I prefer is TRIMSPA®, available from Vitamerica, Inc., Cedar Knolls, N.J.

Acquire a cigarette cessation product containing the herb lobelia, which aids any withdrawal that some may experience. Lobelia is a natural herb that tricks the body into thinking it is nicotine, but it does not have the side effects. In the preferred embodiment of my invention, I recommend CIGSATION™, available from Vitamerica, Inc., Cedar Knolls, N.J.

Cut back on drinking coffee and other caffeinated beverages. Sometimes the stress or anxiety that quitters experience is due to the physiological effects of caffeine on the nervous system and not due to withdrawal from nicotine. Try drinking decaffeinated tea or some other warm decaffeinated beverage. Drinking a hot tea provides the same psychological effect as drinking hot coffee.

Eat healthy, nourishing, non-processed foods and take a good vitamin supplement. Remember, the 200+ toxins in cigarette smoke have helped deplete the body of vitamins. Five cigarettes can deplete all the vitamin C in the body! By eating a healthy diet, you will recover your health more quickly.

In my preferred embodiment, the smoker is educated to do this for at least the first week, preferably for the first 21 days, after stopping smoking:

Eat 3 meals a day, including breakfast

Have protein and complex carbohydrates with each meal

Avoid sugar

Drink 8 glasses of non-caloric liquids a day—drink water with lemon, seltzer, herbal tea, etc.

Keep a pitcher of water on your desk and you'll easily drink 8 glasses a day

Between meals, drink fruit juices or eat a piece of fruit

Eat lots of fruits, vegetables and salads

As soon as you finish eating, leave the table and go brush your teeth

Use mouthwash whenever possible

In my preferred embodiment, the smoker is admonished: to not skip any meals (and never miss breakfast); to limit refined-sugar intake (and read packaging labels); to avoid beverages with caffeine (tea, colas, coffee, hot chocolate); and, if you must have them, drink tea or coffee out of a juice glass using a straw; and NO alcohol.

We described above the change in blood sugar levels caused by smoking and the physical and emotional response it has on the body. If your blood sugar level gets low, you will either crave a cigarette or something sweet. In either case, it will boost your blood sugar level for 10 to 20 minutes and then cause a crash, triggering another urge for a cigarette or a sweet. By eating 3 meals a day, you will tend to have a stable blood sugar level, and this minimizes cigarette and eating urges. Eating protein with carbohydrates at breakfast sets the stage for stable blood sugar levels all through the day. Protein with complex carbohydrates stabilizes the blood sugar.

I have also found it useful to teach persons quitting smoking to carry a nonfood item such as a swizzle stick or a low calorie food such as celery or carrot sticks. Use these to gratify any oral habit that has been developed by the conditioned response of putting your hand to your mouth 250 times a day, as if you were a one pack a day smoker.

By providing the smoker with this kind of educational program, the smoker is able to consciously and analytically understand their need to smoke and to approach the decision to smoke, or to not smoke, in an analytical, dispassionate manner.

Hypnosis. In addition to the conscious, analytical mind, one can aid the stop-smoking process by using the subconscious mind. In my invention, it is important to use both the conscious mind—via the educational program discussed above—and the unconscious mind, with hypnosis.

The subconscious mind dominates your thinking and behaviors. It is programmed using repetition and the subconscious mind basically behaves for two reasons. It tries to take you towards pleasure and it wants you to stay away from pain. For example, when you have a cup of coffee, you grab a cigarette; you get into a car, you grab a cigarette; you get stuck at a light, you grab a cigarette; you get a break at work, you grab a cigarette; you have a cocktail, you grab a cigarette. If you do not experience these triggers, you may very often go many hours without having a cigarette. It is important that you identify these scenes so we can then break the connection of the cigarettes to the scenes.

With hypnosis, the subconscious mind no longer aids the body to smoke more often, but rather aids the body to stop smoking, during precisely those periods when a smoker is accustomed to having a cigarette. Instead of the subconscious making the body scream for nicotine after a meal, or with coffee or alcohol, the subconscious will help the smoker remain calm and pain free.

When used to stop smoking, I have found that in my preferred embodiment, the hypnosis focuses on interrupting "conditioned responses" generally, and specifically, on interrupting the response to smoke. Conditioned responses are actions (e.g., reaching for a cigarette) motivated not by a consciously-perceived need, but rather by unconscious habit.

Is smoking more of a physical or more of a psychological addiction? For example, how many times have you gone two, three or four hours without even smoking one cigarette and then in another hour you may smoke four, five or six cigarettes? Why is that? It is because certain events, or certain times of the day can trigger you to smoke a cigarette. Therefore, it is necessary to break these unconscious connections, and such breakage occurs, I found, most efficiently using unconscious means—hypnosis.

In my preferred embodiment of my invention, the hypnosis is done in-person and is reinforced later with prerecorded media such as audio-tapes.

Hypnosis techniques are known in the art. In my preferred embodiment, I prefer the in-person hypnosis to follow a six-step protocol. The six steps are (1) neuro-linguistic programming, (2) physical positioning, (3) progressive relaxation, (4) occupying the critical/analytical factor, (5) a process of suggestion, and (6) changing the language of the subconscious.

(1) Neuro-linguistic programming is a technique known in the art. It is described in detail in the following works written since the 1960's.

*The Structure of Magic*, Vol.1—Richard Bandler/John Grinder

*The Structure of Magic*, Vol.2—Grinder/Bandler

*Patterns of Hypnotic Techniques of M. H. Erickson*, Vol.1 Bandler/Grinder

*Patterns of Hypnotic Techniques of M. H. Erickson*, Vol.2 Grinder/Bandler

*Frogs Into Princes*—Bandler/Grinder

*Tranceformations*—Grinder/Bandler

*Using Your Brain for a Change*—Richard Bandler
*Time for a Change*—Richard Bandler
*Persuasion Engineering*—Richard Bandler/John La Valle
*The Adventures of Anybody*—Richard Bandler
*Science and Sanity*—Alfred Korzybski
*Uncommon Therapy*—The Psychiatric Techniques of Erickson—Jay Haley
*Training Trances*—John Overdurf/Julie Silverthorn
*My Voice Will Go With You*—Sidney Rosen These are incorporated herein by reference.

(2) Physical positioning is important, to maintain the subject in a state which is both relaxed, yet not sleep-prone.

(3) Physical Positioning and Progressive Relaxation follow the methods known in the art, instructing the subject to progressively relax each part of their body. This can be done with instructions to, for example, physically perform some act, or to mentally visualize some relaxing phenomenon.

(4) Occupying the critical/analytical factor is accomplished in my preferred embodiment by having the subject perform certain tasks which both require some conscious attention, but also are not so difficult or complex as to absorb the subject's entire mental capacity.

(5) The process of suggestion is important to repeat for an effective period of time—usually at least daily for about twenty one days. This time may, however, be less when the subject is relaxed, or is in a highly-emotional state.

(6) The last step is changing the language of the subconscious. This is done by repeating a desired message—e.g., "I am free from smoking"—often enough that the desired message replaces an undesired message in the subconscious mind. For example, one technique is to get friends, coworkers, and family members to help you, by asking them to congratulate you for not smoking. The best way to accomplish this is to stick your hand out to a friend or family member, asking that person to shake your hand and congratulate you for being a nonsmoker. When that person congratulates you, it is a positive reinforcement. The (former) smoker benefits from this positive feedback, and from knowing that they are doing well in stopping smoking.

In another technique I found successful, smoking is described as like having a best friend. Psychologically, the cigarette is the support that a friend gives you. Imagine having your best friend there for you and then losing him or her. You would not feel very good losing your best friend. However, if you discover that your best friend was abusing your children, most likely you would not feel the same about losing your best friend. You would still have some sort of attachment, but now you would be able to reason your way out of not having this person as a friend. In my preferred embodiment, the educational program teaches smokers to look at smoking in the same way.

In my preferred embodiment of my invention, hypnosis is also administered by listening to a prerecorded audio script which provides stop-smoking messages and positive feedback for not smoking. Such audio tapes are commercially available. In my preferred embodiment, I use an audio tape titled "Smoking Cessation," published by Vitamerica, Inc. Cedar Knolls, N.J., www.vitamerica.com, to be listened to once every day for an effective length of time, generally about twenty-one days.

Dietary Substances. The third element of my invention is using proper dietary substances. These address the physiological needs of people breaking their physical addiction to nicotine. Further, one of the biggest fears of smokers is that, in stopping smoking, they will gain excess weight. Thus, in my preferred embodiment, in addition to the dietary substances that support normal form and function while recovering from a smoking addiction, one also uses dietary substances that support normal form and function for those seeking weight-loss or to reduce weight gain. In my preferred embodiment, I recommend CIGSATION™ and TRIM SPECIFICS™, dietary supplements by Vitamerica, Inc., Cedar Knolls, N.J., www.vitamerica.com.

To aid the reader's understanding, I will discuss first the biological basis of the smoking addiction. I will then discuss the dietary substances and the diet modifications I have found effective to combat the physical smoking addiction—the addiction to nicotine. Finally, I will discuss dietary substances to control weight gain.

What causes the addiction to nicotine? The nervous system is divided into two anatomical divisions. The first is the central nervous system, which is composed of the brain and spinal cord. The second is the peripheral nervous system, which includes neurons located outside the brain and spinal cord, which includes any nerves that enter or leave the central nervous system. The peripheral nervous system can be further divided into the efferent division, whose neurons carry signals away from the brain and spinal cord to the peripheral tissues, and the afferent division, whose neurons bring information from the periphery to the central nervous system.

Nerve impulses are transmitted along a path of cells called neurons. The neurons form a knot-like mass called ganglia. These neurons are connected by a series of bridges. The bridge is called a synapse. In order to dross the bridge, a neurotransmitter is required. Before the nerve impulses reach the relay station or bridge, they are referred to a pre-ganglionic neurons. After crossing the synapse, they are referred to as post-ganglionic neurons. The basic neurotransmitters of the autonomic nervous system are acetylcholine and epinephrine. Acetylcholine mediates the transmission of nerve impulses across autonomic ganglia in both the sympathetic and parasympathetic nervous systems.

Nicotine Receptors. These receptors, in addition to binding acetylcholine, also recognize nicotine. Nicotine initially stimulates and then blocks the receptor. There is a competitive inhibition taking place. In lay terms, the receptor has a greater affinity for nicotine than for acetylcholine. At the same time, nicotine increases the level of the neurotransmitter dopamine in a particular brain pathway which associates a molecular link between nicotine addiction and this pleasure producing pathway. This is why nicotine causes such as strong physiological addiction. Recently, scientists at Yale and at the Pasteur Institute in Paris have found that the beta 2 sub unit of a known nicotine receptor in the brain is a critical component in nicotine addiction.

To combat this nicotine addiction, it is useful to use lobelia. *Lobelia inflata* (also known as Indian Tobacco) is a plant. This plant contains three nicotine-like ingredients : 1) lobeline, 2) lobelanidine, and 3) lobelanine. On close inspection of these three ingredients one can notice that all are symmetrical molecules. In other words, if you cut them each in half, each half is the same. The only exception is with lobeline, which has a slight difference on one side of the molecule. I refer to each of these three compounds, their analogs, and derivatives, as "lobelia." After explaining some basic physiology, you will see why lobelia is important.

Nicotine causes an increase in blood pressure, increases intestinal motility, stimulates the central nervous system, has an anti diuretic effect (ability to retain water), affects heart rate, affects respiration, is highly soluble and crosses the blood-brain barrier, produces some euphoria (feeling of well being), arousal, relaxation, and it improves attention, and crosses the placenta membrane and is secreted in the milk of lactating women. The chronic effects of Nicotine include nasopharyngeal and bronchial irritation, lung cancer, cardiac irregularities, stimulated salivary secretion, and reduction of gastric acidity.

Let us now consider the structural formulas for the active constituents in lobelia. Because of their basically symmetrical structure, it appears that they have an advantage in competing with nicotine at the effector cell site. It is postulated that these components can attach themselves to the cell site from either side of the molecule and perhaps crowd out the nicotine. Later, after the nicotine is eliminated from the system, lobeline will replace nicotine at the effector cell site. While nicotine is rapidly eliminated from the body within 16–24 hours, the withdrawal symptoms can last for several weeks to several months, depending upon the individual.

Lobelia's action in the body mimics that of nicotine, but does not have the physiological dependence of nicotine. Lobelia exhibits a cross tolerance with nicotine, is one of the most useful systemic relaxants, has a relaxation effect on the central nervous system, has a relaxing action on the autonomic nervous system, has a general relaxing action on neuromuscular action, is a powerful respiratory stimulant, equalizes circulation and relieves vascular tension, provides a truly holistic action with a combination of stimulation and relaxation, and also provides the holistic action of a general relaxant with diffusive stimulation.

Recently, scientists in Japan have discovered an antidepressant component in the leaves of *lobelia inflata*. This probably explains why individuals feel better when taking lobelia.

Given this physiology, the physiologic needs of a smoker can be addressed using lobelia. In addition to lobelia, I have found that other herbal substances are useful as dietary substances. Thus, in my preferred embodiment, lobelia is used along with wood betony, fennel seed and licorice root and several other herbs. In addition to these vitamin-type nutritional supplements, in my invention one needs lobelia. Lobelia is also known as Indian tobacco or wild tobacco and is native to North America. It includes three components significant here: lobeline, lobelanidine and lobelanine. It is pharmacologically similar to nicotine, but does not have nicotine's physiological dependency.

In my preferred embodiment of my invention, I have found it beneficial to include certain other supplements derived from plants and herbs. Each the individual ingredients improves the function of lobelia alone, as each provides a specific function to enhance the efficacy of the product.

Wood Betony. Wood betony is used for its sedative and bitter properties. Its anti-hypertensive properties relieve nervous tension and dilate blood vessels, thus producing a calming effect. Wood betony can relieve headaches normally associated with nicotine withdrawal. Its bitter tonic properties also aid in nicotine withdrawal.

Fennel Seed. Fennel seed has been recognized to have carminative and stimulant properties. It has been reported to have a spasmolytic effect on smooth muscles. As a result, it can be used for dyspeptic discomfort, gastrointestinal discomforts and congestion of the upper respiratory tract. Since chain smokers normally have a smoker's cough resulting in congestion of the lungs, fennel seed can aid in treating that congestion. One of the constituents from the volatile oil expressed from fennel is anethol. Anethol has been shown experimentally to reduce secretions of the upper respiratory tract (i.e., lungs).

Licorice Root. The major active ingredient in licorice root is glycyrrhizin. The glycyrrhizin is responsible for a vasopressor response, which is similar to that occurring in nicotine. However, while it mimics that response, it also exhibits anti-inflammatory and an antitussive effects that is comparable to codeine in potency. This is due to the derivative 18 Beta-glycyrrhetinic acid which prevents smoker's cough. In addition, the flavonoids in licorice root have recently been shown to have strong antioxidant and anti-hepatotoxic activities. These activities will help cleanse the body of the free radicals and other toxic substances generated from smoking. Licorice extracts are often used in anti-smoking preparations as a flavoring agent to mask bitter nauseous or other undesirable tastes from other components of the preparation. Licorice can also be used to treat stomach irritation arising from nicotine usage.

In addition to the foregoing, I have found it useful to use also blue cohosh, black walnut husk, chamomile flower, gotu kola leaf extract, kava kava root, peppermint, sarsaparilla root, slippery elm bark, valerian root, bayberry fruit, myrrh, passion flower, ginger root and eucalyptus oil. Thus, in my preferred embodiment, I use each of these, for the following reasons.

Blue Cohosh. It has demonstrated anti-inflammatory activity in animals. Blue cohosh can be used for nervous disorders.

Black Walnut Husk. Black walnut husk is a blood cleanser and oxidizer. It has been shown to be useful in lung disease and has strong anti-fungal and antibacterial properties. It is a rich dietary source of protein, iodine, chromium, potassium, manganese, vitamin A and the powerful antioxidant vitamin C.

Chamomile Flower. Chamomile flower has essential oils that contain a variety of glycosides, and other important constituents and chemically related compounds. Several of the therapeutic constituents of the volatile oil are chamazulene and alpha bisabolol oxide A. Chamazulene has demonstrated anti-inflammatory activity, pain relieving, wound healing, antispasmodic and anti-microbial properties. Alpha bisabolol has anti-inflammatory, anti-microbial and anti-peptic activities. Matricin has been found to have a sufficiently stronger anti-inflammatory effect than chamazulene.

Gotu Kola Leaf Extract. The gotu kola leaves contain properties that have been shown to accelerate wound healing, improve memory, relieve fatigue and stress, increase mental acuity and improve behavioral patterns. This produces a calming effect within the body, thereby relieving the stress associated with nicotine withdrawal symptoms.

Kava Kava Root. The active ingredients in kava kava root are a group of compounds known as the kavalactones. They are recognized for their biological activity as a sedative, anti-convulsive and tonic. Additional constituents in kava kava root have demonstrated muscle relaxant activity and have been used for their ability to combat nervous anxiety and unrest. Kava kava also has expectorant properties. This allows the heavy smoker to expectorate residual mucus from the lungs.

Peppermint. Peppermint yields a volatile oil that is composed mainly of menthol. Menthol has long been recognized as a cooling agent in topical preparations. Also present are many other ingredients, some of which have been characterized to have biological activity. One such constituent is bisabolene, which has demonstrated to have anti-inflammatory activity. Other constituents in peppermint include flavonoids such as hesperetin and rutin. Also present are tocopherols, carotenoids, choline and azulenes. Azulene isolated from peppermint demonstrated anti-inflammatory and antinuclear effects in experimental animals. Peppermint oil is extensively used as a flavoring agent, carminative, antiseptic and local anesthetic in cold, cough and other preparations. Peppermint and their oils have been used in traditional medicine as a stomachic, stimulant, antiseptic, local anesthetic and antispasmodic in treating indigestion, sore throat, nausea, diarrhea and colds.

Sarsaparilla Root. The major component of sarsaparilla is a variety of steroids which include sarsasapogenin, smilagenin, sitosterol, stigmasterol and pollinastanol, and their glycosides (saponins) including sarsasaponin (parillin), smilasaponin (smilacin), sarsaparilloside and sitosterol glucoside. Sarsaparilla is reported to have hepatoprotective, diuretic and anti-inflammatory activity.

Slippery Elm Bark. The principal constituent of slippery elm bark is mucilage. The mucilage has demulcent (soothing) and nutritive properties. It can sometimes be used to soothe irritated lungs.

Valerian Root. Valerian root has a variety of constituents but the major one, valerenic acid, produces a nerving or sedative effect. Valerian has CNS depressant activities. As a result, in states of agitation normally witnessed by smokers during withdrawal, this will have a calming effect. It has also been shown that in conditions of fatigue, the herb has demonstrated stimulating properties.

Bayberry Fruit. Bayberry fruit has been recognized to have a tonic effect.

Myrrh. Myrrh is reported to have astringent effects on mucus membranes. It is often used as a flavor component to mask bitter ingredients. It has also been used as a stimulant and expectorant. The expectorant properties will help the smoker remove mucus and phlegm from the lungs.

Passion Flower. Passion flower contains indole alkaloids, flavonoids and steroids. The indole alkaloids and flavonoids have tranquilizing effects. Anxiolytic and hypotensive activity has also been reported.

Ginger Root. Ginger root is used to combat nausea and vomiting, which may accompany nicotine withdrawal.

Eucalyptus Leaf Oil. The leaves contain 0.05 to 3.5% oil. The oil consists mostly of eucalyptol (1, 8-cineole). It is used in an anti-smoking formula as an expectorant to help remove mucus from the lungs.

In my preferred embodiment of my invention, these dietary substances are used as found in CIGSATION™ 100% Natural Cigarette Replacement System, commercially available from Vitamerica, Inc., Cedar Knolls, N.J. 07927, www.vitamerica.com. Each of these dietary substances adds to the benefit obtained from using lobelia alone.

In addition to addressing the physical nicotine addiction, I find it useful to address the smoker's fear of excessive weight gain, by using a "weight control product," a drug or dietary substances useful in controlling unnatural weight gain. Such dietary substances include chromium, choline, inositol, vanadium, gynema sylvestre, lecithin, vitamin B6, ginseng, zinc, mahuang, kola nut extract, spirulina, and methionine. Several of these are known physiological stimulants, which increase thermogenesis in the body and thus promote expending calories. I will discuss each in turn, and its usefulness in a weight-control product.

Chromium. What is chromium? It's the mineral that no body can afford to be without. Like iron, copper and zinc, chromium is one of the 16 essential trace minerals the body needs to keep healthy and fit. And for people who are overweight and out of shape, chromium may be the most precious mineral of all. In its biologically active form, it helps insulin to metabolize fat, convert protein into muscle, and convert sugar into energy. Chromium-activated insulin actually increases almost twenty times the amount of glucose available for energy production, optimizing energy output so that you feel healthy and alive.

Chromium is the "master" nutrient for controlling blood sugar. It helps overcome sugar cravings, which is a problem with many overweight people. It also plays an important role in controlling blood lipids, lowering harmful LDL cholesterol, and increasing beneficial HDL cholesterol.

Research shows that a chromium deficiency may be a widespread problem. Many people, such as athletes, diabetics, mothers and the elderly, are at especially high risk. A lack of chromium can impair insulin function, thereby inhibiting protein synthesis and energy production. More seriously, it can even lead to type II diabetes and heart disease.

In my preferred embodiment, the chromium is a form of chromium commercially available under the trade name CHROMIUM CHELAVITE™, available from Vitamerica, Inc. of Cedar Knolls, N.J.

The most biologically active form of chromium, the true GTF chromium, is the basis for the molecular structure of CHROMIUM CHELAVITE™. Studies on CHROMIUM CHELAVITE™ at a leading Utah university have shown that this form of chromium is clearly superior to both chromium picolinate and chromium polynicotinate in absorb ability. It had an absorption rate that was 53% greater than for chromium picolinate and 91% greater than that observed for chromium polynicotinate.

Choline. Choline is one of the most beneficial nutritional supplements. Technically, it is not a vitamin, even though it is essential for human life. There are three major functions of choline among humans. It is needed for building cell structure, it prevents or minimizes unhealthy fat deposits in the liver, and it acts as a precursor to acetylcholine. Acetylcholine is a neurotransmitter in the brain which is responsible for nerve impulses, memory, learning, mood elevation and depression control.

Choline has a very positive effect on the health of the liver. It is a lipotropic agent (fat eliminator) that can cut away fats in the liver to be used instead of energy. Choline aids in weight loss by facilitating Growth Hormone (GH) releasers, controlling cholesterol, and helping control the appetite. It also helps reduce the "gut transit time", the amount of time it takes food to move through the intestines. In addition to helping speed food through the system, choline also plays an important role in the body's ability to metabolize fat and cholesterol.

Inositol. Inositol is a member of the B complex of vitamins. It provides a calming effect, nourishes brain cells, helps reduce cholesterol, slows artery hardening, prevents eczema, and is needed for hair growth and metabolism. It is found in high concentrations in the brain, and serves as a brain cell membrane stabilizer. Inositol also helps in lecithin formation, and aids the body in the metabolism of fat and cholesterol.

Vanadium. A trace mineral like chromium, vanadium is essential for cellular activity and for the formation of bones and teeth. It also inhibits the synthesis of cholesterol and lowers certain forms of high blood pressure. It works remarkably well as a powerful insulin mimic and has been shown to normalize blood sugar levels, even in diabetics.

Gynema Sylvestre. This tropical herb is beginning to receive much attention due to impressive results in recent studies. Gynema Sylvestre appears to have a positive effect in lowering blood sugar levels, especially in diabetics. Research also suggests that it can help curb sugar absorption.

Lecithin. Lecithin is part of every single cell in the body, but has its greatest concentration in the brain. About 17–20% of the brain is made up from lecithin. Lecithin is an emulsifier. It is used in the manufacture of chocolate, because it keeps it liquid and it keeps it moving. Lecithin does the same thing for the fat in the human body; it keeps it moving, right out of the body.

Lecithin is a natural diuretic and an effective cholesterol reducer. It helps prevent the buildup of cholesterol on arterial walls, thus improving the circulation of the blood. One study that examined 900 men for atherosclerosis (fat deposits in the arteries) showed that those with more than 36% lecithin in the blood had no atherosclerosis. Those with less than 34% showed evidence of the disease.

Lecithin is also the source of two of the hardest to find B-Complex relatives, choline and inositol. A major function of lecithin is to supply choline in the diet. Choline (see entry) has the function of breaking down fat deposits in the body. Our bodies do not manufacture enough choline. Therefore, we must rely upon our food and supplements such as lecithin to make sure that we get enough.

Vitamin B6. Vitamin B6 aids in more bodily functions than any other single nutrient. It facilitates the body's use of carbohydrates, proteins and fats. It promotes mental performance by aiding in the transport of amino acids, which are used by the brain to increase mental energy and memory. It also promotes the transport of choline, and aids in the breakdown of glycogen, the primary fuel for the brain.

Ginseng. For centuries, the Chinese have testified to the beneficial effects of Ginseng on longevity. Ginseng provides stimulation to the entire body, helping to overcome stress and fatigue. Ginseng can regulate and normalize blood pressure and blood sugar levels. It has been called a cure-all and has also been claimed to be a mild sexual stimulant. Over all, Ginseng has a phenomenal effect on the body's energy level.

Zinc. Zinc is another important trace mineral that is used by more than 200 enzymes to keep the body's major metabolic systems going strong. In addition to its role in metabolism, zinc is a potent antioxidant, profoundly important in enhancing the immune system, stimulating cellular growth, reducing excess levels of damaging free radicals, and improving general health.

Mahuang. Mahuang, also known as ephedra, contains a potent alkaloid, ephedrine. This natural stimulant increases the basal metabolic rate, which helps to burn calories more effectively. It has also been used as a remedy for kidney and bladder problems, as well as for colds, asthma, and hay fever.

Kola Nut Extract. This is a natural stimulant that increases energy and stamina. It has been found to be very useful in preventing fatigue. Kola Nut Extract also acts as a tonic agent for the heart, and it is sometimes useful in relieving pain, neuralgia, and headache.

Spirulina. This famed blue-green algae contains concentrations of nutrients unlike any other single grain, plant or herb. This super nutrient is a naturally digestible food that aids in protecting the immune system, in cholesterol reduction and in mineral absorption. It also helps to cleanse and heal, while also curbing the appetite.

Methionine. Methionine is an amino acid that assists the gall bladder function by helping to synthesize bile salts. It is a lipotropic substance that prevents the deposits of and cohesion of fats in the liver. It is also reported to be a growth hormone releaser.

It serves as an antioxidant in the brain. It helps prevent the buildup of heavy metals and plays an important and essential role in the production of the brain neurotransmitter choline. Methionine is not found in the body. Therefore, it must be gotten via food and supplementation. It is also a good source of sulfur, and its therapeutic lipotropic effects help to eliminate fatty substances from the body.

Each of these dietary substances can be found in TRIM SPECIFICS™, available from Vitamerica, Cedar Knolls, N.J., www.vitamerica.com.

Without further elaboration, it is believed that one skilled in the art can, using the preceding description, utilize the present invention to is fullest extent. The examples I discuss here are included as the preferred embodiment of my invention, and not to further qualify the description.

I claim:

1. A method for helping a tobacco smoker to stop smoking, said method comprising the steps of:
   (A) providing to a tobacco smoker a non-conditioning, educational program to educate said tobacco smoker's conscious mind, said educational program including education both on the disadvantages of smoking and on conscious techniques to stop smoking,
   (B) providing to said tobacco smoker at least one hypnosis program to train said tobacco smoker's subconscious mind to discourage said tobacco smoker from performing smoking behavior, and
   (C) providing to said tobacco smoker an anti-smoking drug in an amount effective to aid in the reduction or cessation of said tobacco smoker's craving to smoke tobacco,
   such that said tobacco smoker can be helped to stop smoking.

2. The method of claim 1, where said hypnosis program comprises prerecorded media useable by said tobacco smoker when alone.

3. A product to aid a tobacco smoker in ceasing to smoke tobacco, said product comprising:
   (A) means for educating said tobacco smoker's conscious mind, said educational program including non-conditioning education both on the disadvantages of smoking and on conscious techniques to stop smoking,
   (B) means for hypnosis to train said tobacco smoker's subconscious mind to discourage said tobacco smoker from performing smoking behavior, and
   (C) an anti-smoking drug in an amount effective to aid in the reduction or cessation of said tobacco smoker's craving to smoke tobacco.

4. The product of claim 3, where said means for hypnosis comprises prerecorded media useable by said tobacco smoker when alone.

5. The method of claim 1, further comprising the step of:
(D) providing to said tobacco smoker, at least one weight-control product, in an amount effective to aid in weight control.

6. The method of claim 5, where the weight control product includes at least one stimulant in an amount effective to aid in weight control.

7. The product of claim 3, further comprising: (D) at least one weight-control product in an amount effective to aid in weight control.

8. The product of claim 7, where the weight control product includes at least one stimulant in an amount effective to aid weight control.

\* \* \* \* \*

UNITED STATES PATENT AND TRADEMARK OFFICE
CERTIFICATE OF CORRECTION

PATENT NO.    : 6,431,874 B1
DATED         : August 13, 2002
INVENTOR(S)   : Alexander G. Szynalski It is certified that error appears in the above-identified patent and that said Letters Patent is hereby corrected as shown below:

Column 12,
Lines 26-27 and 45, delete each occurrence of "an anti-smoking drug" and insert at each occurrence -- lobelia --.

Signed and Sealed this

Eighteenth Day of November, 2003

JAMES E. ROGAN
*Director of the United States Patent and Trademark Office*

EX PARTE REEXAMINATION CERTIFICATE (5362nd)
United States Patent
Szynalski

(10) Number: US 6,431,874 C1
(45) Certificate Issued: May 2, 2006

(54) STOP SMOKING METHOD AND COMPOSITION

(75) Inventor: Alexander Goen Szynalski, Randolph, NJ (US)

(73) Assignee: Goen Corporation, Cedar Knolls, NJ (US)

Reexamination Request:
No. 90/006,704, Jun. 30, 2003

Reexamination Certificate for:
Patent No.: 6,431,874
Issued: Aug. 13, 2002
Appl. No.: 09/427,447
Filed: Oct. 27, 1999

Certificate of Correction issued Nov. 18, 2003.

(51) Int. Cl.
*G09B 23/28* (2006.01)

(52) U.S. Cl. .................................... 434/262
(58) Field of Classification Search ............ 434/262; 514/282, 343; 424/449
See application file for complete search history.

(56) References Cited

U.S. PATENT DOCUMENTS

| | | | | |
|---|---|---|---|---|
| 5,332,579 A | * | 7/1994 | Umbdenstock | 424/639 |
| 5,599,554 A | * | 2/1997 | Majeti | 424/448 |
| 5,798,101 A | * | 8/1998 | Haveson | 424/730 |
| 6,166,032 A | * | 12/2000 | Viner | 514/316 |
| 6,224,873 B1 | * | 5/2001 | Jones | 424/736 |

OTHER PUBLICATIONS

Nicotine Dependence: Americas Drug of Choice—Linda H. Ferry 1998.*
Goen "Stop Smoking with Hypnosis in Just 2 Hours" advertisement © 1995.*
Goen Seminars Stop Smoking Workbook © Goen Seminars 1995.*
Gorayeb "Stop Smoking with Hypnosis in Just 2 Hours" advertisement © 1995.*
Gorayeb Seminars Stop Smoking Workbook © Gorayeb Seminars, Inc. 1996.*

* cited by examiner

Primary Examiner—Jacob K. Ackun, Jr.

(57) ABSTRACT

The inventor discloses a unique, new and useful process to reduce tobacco smoking, entitled Stop Smoking Method and Composition, consisting of: (1) educating tobacco smokers regarding smoking, its physiological dangers and addictive nature, and techniques to stop smoking; (2) hypnotizing said tobacco smokers, and (3) providing dietary substances to address the nutritional needs of nicotine addiction and the nutritional challenges thereof.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–8 are cancelled.

* * * * *